US00PP14176P39

(12) United States Plant Patent
Kordes

(10) Patent No.: US PP14,176 P3
(45) Date of Patent: Sep. 23, 2003

(54) HYBRID TEA ROSE PLANT 'KORJAFIR'

(75) Inventor: Wilhelm Kordes, Rosenstrasse 54, Klein Offenseth-Sparrieshoop D-25365 (DE)

(73) Assignee: Wilhelm Kordes, Klein Offenseth-Sparrieshoop (DE)

( * ) Notice: Subject to any disclaimer, the term of this patent is extended or adjusted under 35 U.S.C. 154(b) by 0 days.

(21) Appl. No.: 10/237,926

(22) Filed: Sep. 10, 2002

(65) Prior Publication Data

US 2003/0163859 P1 Aug. 28, 2003

(51) Int. Cl.[7] ..... A01H 5/00

(52) U.S. Cl. ..... Plt./137

(58) Field of Search ..... Plt./137, 135, 130

*Primary Examiner*—Bruce R. Campell
*Assistant Examiner*—Annette H. Para

(57) ABSTRACT

A new and distinct variety of Hybrid Tea rose plant which have attractive magenta-purple colored flowers and attractive dark green and glossy foliage. The buds are large and well turbinated. This new variety is having high production of long stems with a long vase life, vigorous, upright growth, and good tolerance to powdery mildew. The variety successfully propagates from softwood cuttings and is well suitable for year round production of cut flowers in commercial glass houses as a flowering cut rose. This and distinct variety has shown to be uniform and stable in the resulting generations from asexual propagation.

5 Drawing Sheets

Figures 1, 2, 3, 4, 5:
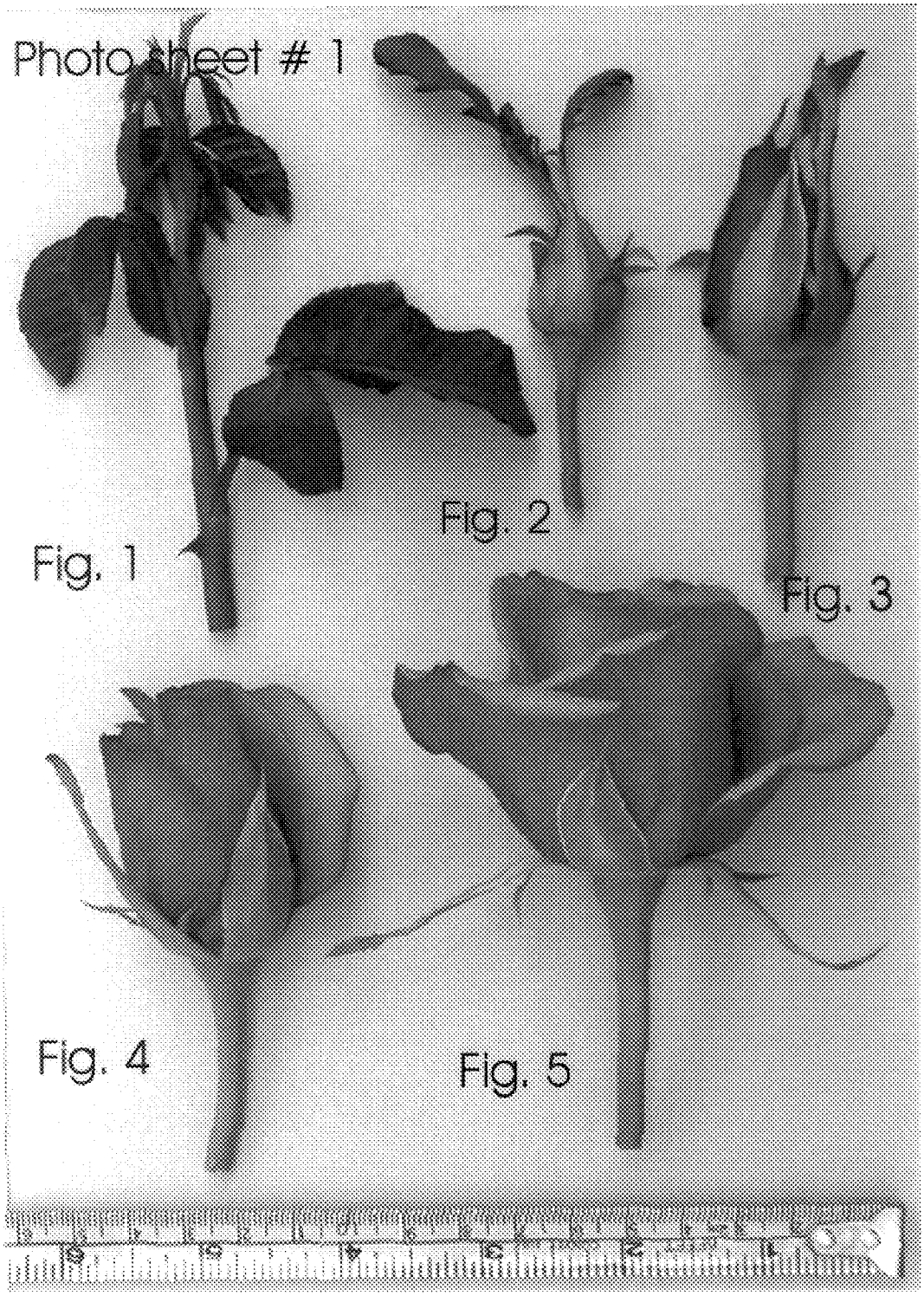

Latin name of genus and species: Rosa hybrid 'KORjafir'.

Variety denomination: The new variety is named 'KORjafir'.

BACKGROUND OF THE INVENTION

The present invention constitutes a new and distinct variety of Hybrid Tea rose plant, which was developed by artificially pollinating an unnamed seedling(not patent in the United States) with an unnamed seedling (not patent in the United States). The two parents were crossed in the summer of 1999 and the resulting seed was sown in December 1999, in a controlled glasshouse environment. Out of these seedlings one seedling was selected, as the new variety and named 'KORjafir'. The new rose may be distinguished from its seed parent, an unnamed seedling, by the following combination of characteristics:

1. The unnamed seedlings has a breeding background in unnamed seedlings.
2. 'KORjafir' has big double flowers, while the unnamed seedling has medium-doubled flowers.
3. 'KORjafir' has dark pink colored petals, while the unnamed seedling has dark red petals.

The new variety may distinguished from its pollen parent, an unnamed seedling created by the same inventor, by the following combination of characteristics:

1. The unnamed seedling has a breeding background in unnamed seedlings.
2. 'KORjafir' has bigger flowers and foliage as compared to the unnamed seedling.
3. 'KORjafir' has dark pink colored petals, while the unnamed seedling has light pink petals.

BRIEF SUMMARY OF THE INVENTION

Initial asexual reproduction of 'KORjafir' by cuttings was first done in Klein Offenseth-Sparrieshoop, Germany. The reproduction was conducted in controlled greenhouse environments. Have here proven to be stabile by propagation with cuttings in several generations.

'KORjafir' is a high productive Hybrid Tea rose with a vaselife of approximately 14 days. 'KORjafir' under conventional greenhouse production ( 18 degree Celcius nights, and 26 Celcius day's) in Germany will produce 170–240 stems per year, averaging 70 cm long.

The objective of the hybridization of this rose variety for commercial greenhouse culture was to create a new and distinct variety with:

1. Uniform and abundant flowers with good vaselife.
2. Attractive long lasting foliage and strong growth.
3. Year round flowering under glasshouse conditions.
4. Suitability for production from softwood cuttings.
5. Durable flowers and foliage which make the variety suitable for distribution in the floral industry.

This combination of qualities was not present in previously available commercial cultivars of this type and distinguish 'KORjafir' from all other varieties of which we are aware.

The seeds from hybridization were planted in a controlled environment and evaluations were conducted on the resulting plants. 'KORjafir' was selected by Wilhelm Kordes in his development program in Klein Offenseth-Sparrieshoop, Germany.

BRIEF DESCRIPTIONS OF THE DRAWINGS

The accompanying color illustrations show as true as is reasonably to obtain in color photographs of this type, the typical characteristics of the buds, flowers, leaves, stems of 'KORjafir'. Specifically illustrated in:

Photo sheet # 1: Young shoot.

FIG. 1. Bud before opening the sepals.

FIG. 2. Bud at the opening the sepals.

FIG. 3. Bud at the opening the petals.

FIG. 4. Flower during course of opening.

FIG. 5. Open flower—plan view.

Figures 6, 7, 8, 9:
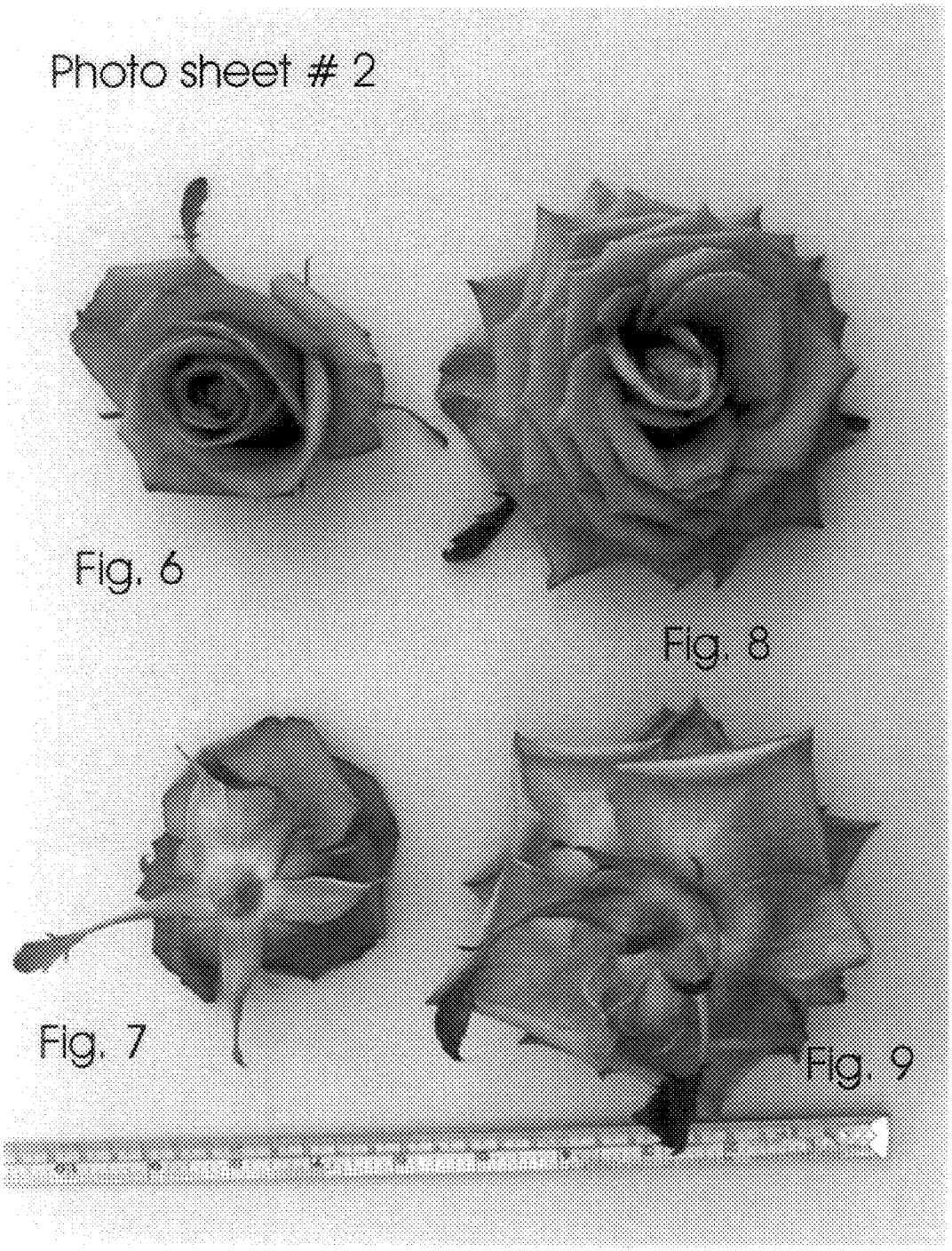

Photo sheet # 2:

FIG. 6. Open flower—plan view—obverse.

FIG. 7. Open flower—plan view—reverse.

FIG. 8. Fully open flower—plan view—obverse.

FIG. 9. Fully open flower—plan view —reverse.

Figures 10, 11, 12, 13, 14:
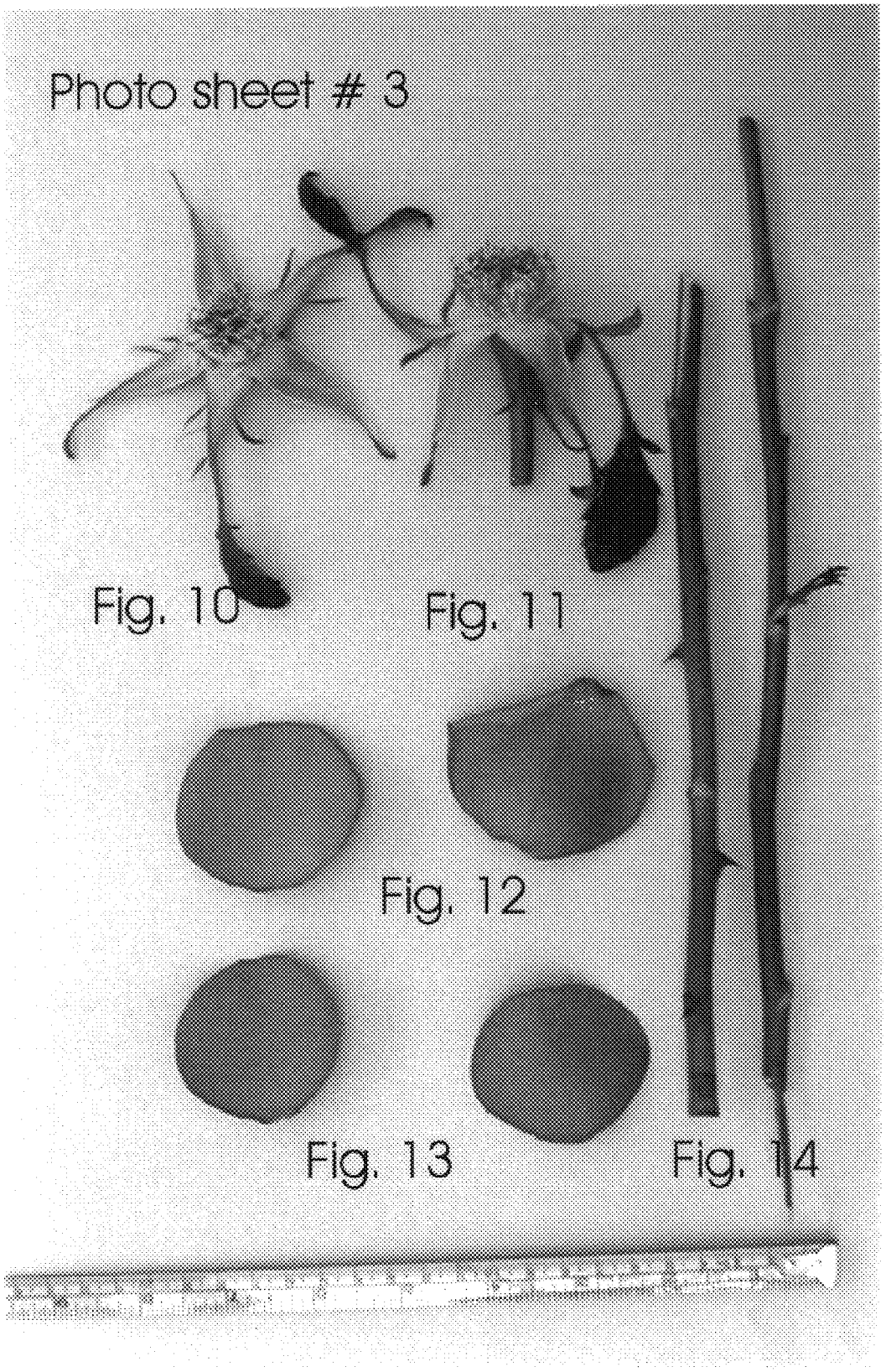

Photo sheet # 3:

FIG. 10. Receptacle showing stamens and pistils.

FIG. 11. Receptacle showing pistils (stamens removed).

FIG. 12. Flower petals, detached—outer surface.

FIG. 13. Flower petals, detached—inner surface.

FIG. 14. Bare stem exhibiting thorns and flower attachment.

Photo sheet # 4

Figure 15:
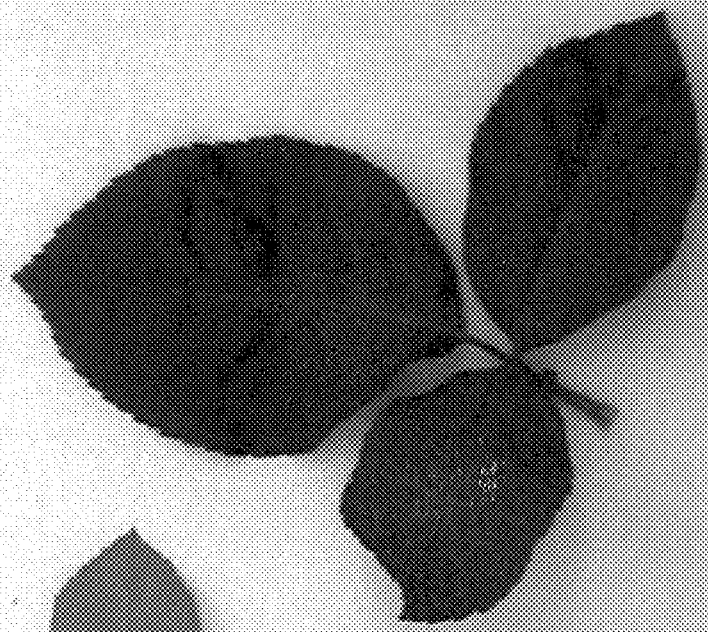

FIG. 15. Three leaflets upper side.

Figure 16:
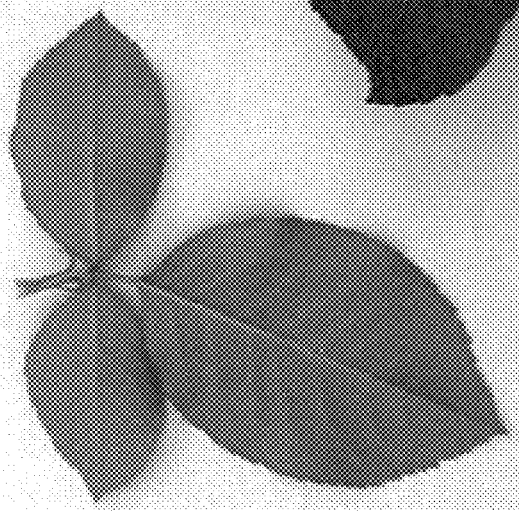

FIG. 16. Three leaflets reverse side.

Photo sheet # 5

Figures 17, 18:
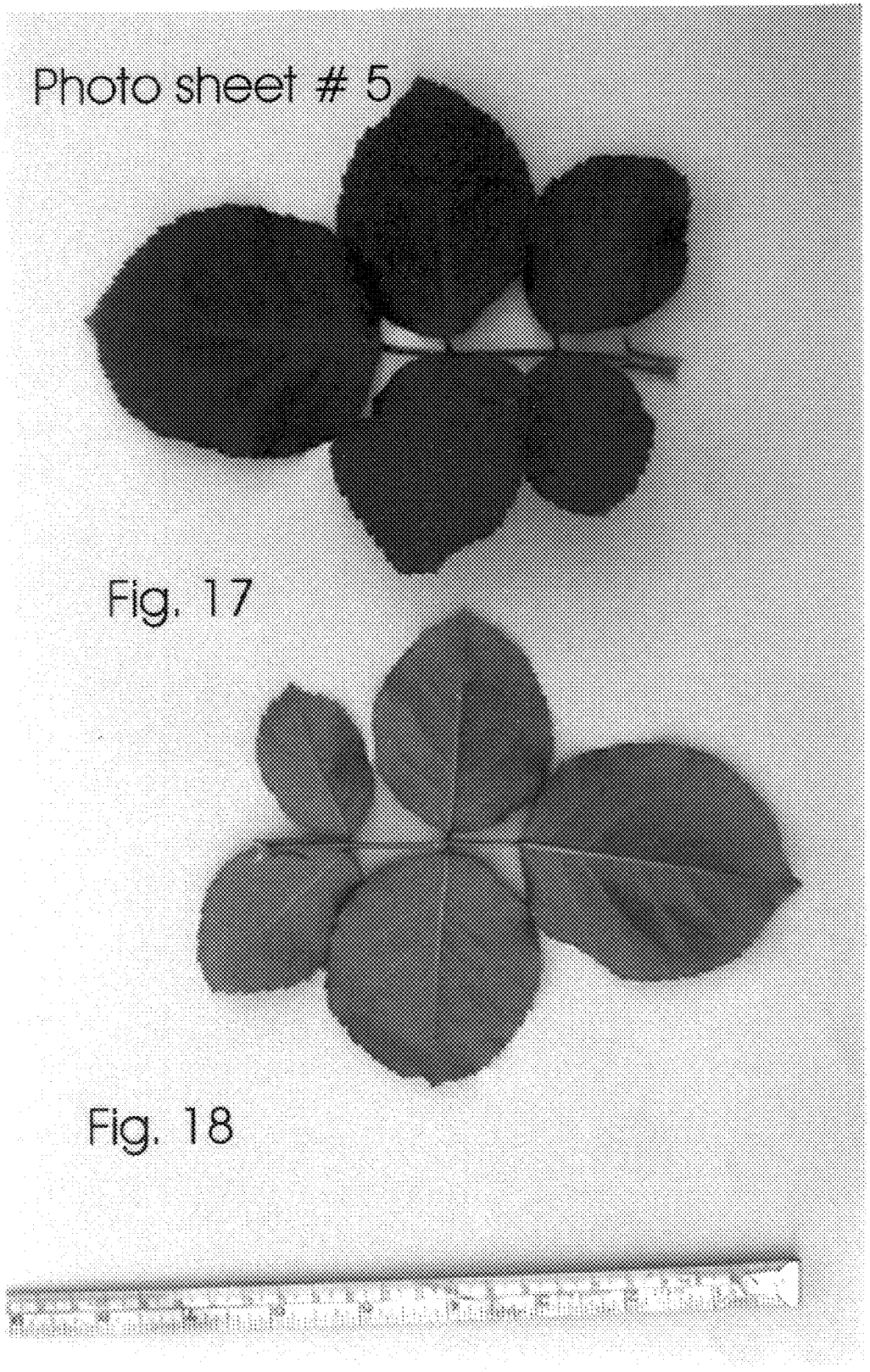

FIG. 17. Five leaflets upper side.

FIG. 18. Five leaflets reverse side.

DETAILED BOTANICAL DESCRIPTION OF THE VARIETY

The following is a detailed description of the Hybrid Tea Rose: Rosa hybrid 'KORjafir'.

The following observations, measurements, values and comparisons describe plants grown in glass houses in Klein Offenseth-Sparrieshoop, Germany. The age of the observed plants where 11 to 13 months after propagation by cuttings, and produced as flowering cut-rose plants.

Color references are made using The Royal Horticultural Society (London, England) Colour Chart, 1995, except where common terms of color are used. For a comparison, the nearest existing rose variety is 'Magic Beauty', a rose variety described and illustrated in U.S. Plant Pat. No. 12,655.

Chart 1 details several physical characteristics of 'Korjafir' and 'Magic Beauty'.

CHART 1

| | 'Korjafir' | 'Magic Beauty' |
|---|---|---|
| Petal color, Upper surface | Red-Purple Group 57-B | Red-Purple Group 74-A on the edge, blending to Red Group 56-C near the middle |
| Petal color, Reverse surface | Red-Purple Group 57-B | Red Group 47-A Blending to Yellow-Orange Group 15-B at the center |
| Petal count | 50–55 | 26–32 |
| Parents | Unnamed Seedling | 'Love' and 'Gold Metal' |

Parents: Unnamed seedling. Times. Unnamed seedling.

CLASSIFICATION

Botanical: Rosa hybrid.
Commercial: Hybrid Tea.

PLANT

Plant growth: Very vigorous. Grows Strong upright to bushy. Production time for floral stems is generally 6 to 8 weeks depending on average temperature, light level and cultural practices.

Height: Plants which were pruned at height of 0.5 meter, produce floral stems having a length of 40 to 90 cm.

STEM

Color:

*Young wood.*—Green Group 143 C with intonations of Greyed-Purple Group 183 C.

*Older wood.*—Green Group 139 A with intonations of Greyed-Purple Group 183 C.

Thorns:

*Incidence.*—High number of thorns.

*Size.*—8–10 mm.

*Color.*—Greyed-Purple Group 183 A with intonations of Green Group 143 D. at the base.

*Shape.*—Deep concave, bending downward.

Surface:

*Young wood.*—Smooth.

*Older wood.*—Smooth.

Stem diameter: 5–8 mm.
Internode length: 50–70 mm.
Numbers of internodes: 10–12.

PLANT FOLIAGE

Leaves arranged alternately, compound with three to seven leaflets per leaf, generally symmetrical, abundant, and flat in aspect. Stipules at petiole base.

Quantity of leaves: 10 to 12 per lateral branch.

*Leaf size.*—Large 60–70 mm(l). times. 40–60 mm(w).

*Petioles.*—Color: Green Group 139 A with intonations of Greyed-Purple Group 183 C. Margins: entire with stipitate glands. Length: 20–25 mm Diameter: about 1–2 mm.

*Stipules.*—Size: 15–20 mm. Surface: Smooth. Color: Green Group 139 B with intonations of Greyed-Purple 183 C. Margins: single, serrated.

*Rachis.*—Color: Green Group 139 B with intonations of Greyed-Purple Group 183 C. Margins: Margins with stipitade glands and thorns on the lower side. Length: 20 to 30 mm.

*Leaflets.*—Edge: Serrated. Serration: Double. Shape: Ovate with abtuse apex and rotundate base. Texture: Smooth. Appearance: Dull. Size: length: 20 to 40 mm. With: 30 to 70 mm. Color: Young foliage: Upper surface: Green Group 143 C with intonations of Green-Purple Group 183 C. Lower surface: Green Group 143 C with intonations of Greyed-Purple Group 183 C. Color: Mature foliage: Upper surface: Green Group 139 A. Lower surface: Greyed-Green Group 189 A.

INFLORESCENCE

Blooming habit: Recurrent.

*Number of flowers.*—Generally 1 bud per flowering stem.

*Peduncle.*—Color: Yellow-Green Group 144 A, Texture: Smooth. Length: 30–40 mm. Strength: Upright,

*Receptacle.*—Surface: Smooth, glabrous. Shape: Funnel-shaped. Size: h: 10–12 mm. w: 12–15 mm. Color: Yellow-Green Group 144 A.

*Sepals.*—Quantity: 5. Shape: Narrowly Ovate w. acute tip. Texture: Leathery. Margin: Foliaceous appendages on 2–3 of the five sepals. Appearance: Dull. Color: Upper surface: Yellow-Green Group 144 A. Reverse surface: Yellow-Green Group 144 D.

*Buds.*—Size: 30–40 mm (h) 25–27 mm (w)upon opening. Shape: Urceolate. Color: at ¼ opening, Red Group 53 C.

Flower:

*Duration.*—As a cutflower, flowers last app. 14 days. Fragrance. Little. Size: 80–100 mm in diameter. Form: Shape of flower when viewed from the side. Up on opening: Cupped. Open flower: Cupped to flat. Color: Petals, upon opening. Upper surface: Red-Purple Group 57 B. Reverse surface: Red-Purple Group 57 B. Petals after opening: Upper surface: Red-Purple Group 57 B. Reverse surface: Red-Purple Group 57 B. Basal Petals spots: Size 5–7 mm. Colour: White Group 155 D. General tonality: On Open flower: Third day: Red-Purple Group 57 A. Afterwards: Red-Purple Group 57 C.

Petals:

*Petal reflex.*—Outermost petals reflex backwards at opening. Fully open all petals reflex backwards.

*Texture.*—Smooth.

*Petal edge.*—Uniform.

*Petal count.*—Approximately 50–55 on the average per flower.

*Petal size.*—Length 50 mm With: 70 mm.

*Shape.*—Outer petals: Round. Inner petals: Round.

Reproductive organs:

*Stamen number.*—Approximately 55–65 on average per flower.

*Pollen.*—Color: Greyed-Orange Group 168 B–C Abundance: Average.

*Anthers.*—Size: 1–2 mm Color: Greyed-Orange Group 168 B–C. Shape: Oblong.

*Filaments.*—Size: 8–10 mm Color: Red-Purple Group 57 A.

*Pistils number.*—Approximately 55–60 on average per flower.

*Stigmas.*—Location: Superior in location to anthers Color: Greyed-Orange Group 163 D.

*Styles.*—Color: Red-Purple Group 66 A. Length: 3 to 5 mm.

DEVELOPMENT

Vegetation: Dense.

Blooming: Abundant.

Aptitude to bear fruit: Poor.

Resistance to diseases: Above average resistance to mildew and Botrytis under normal growing conditions in Klein Offenseth-Sparrieshoop, Germany. Hips/seeds has not been observed due to that the plant has never been grown to the stage of seed development, due to the fact, that the variety is developed for producing floral stems only.

Winter hardiness & drought/heat tolerance: Due to the fact, that this variety is a cut rose plant, developed for producing floral stems only, the plant is not tested for winter hardiness or drought/heat tolerance.

I claim:

1. A new and distinct variety of rose plant of the Hybrid Tea class, substantially as herein illustrated and described as a distinct and novel rose variety due to its abundant magenta-purple colored flowers, attractive long lasting foliage, vigorous and upright growth, year round flowering under glasshouse conditions, suitability for production from softwood cuttings, and durable flowers and foliage which make the variety suitable for distribution in the floral industry.

* * * * *

Photo Sheet # 1

Photo sheet # 2

Photo sheet # 3

Photo sheet #4

Photo sheet # 5